US011839724B2

(12) United States Patent
Jewell

(10) Patent No.: US 11,839,724 B2
(45) Date of Patent: Dec. 12, 2023

(54) ASSISTED CATHETER ADVANCEMENT

(71) Applicant: Becton, Dickinson and Company, Franklin Lakes, NJ (US)

(72) Inventor: Derek Alan Jewell, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/941,817

(22) Filed: Sep. 9, 2022

(65) Prior Publication Data
US 2023/0001147 A1 Jan. 5, 2023

Related U.S. Application Data

(63) Continuation of application No. 17/081,911, filed on Oct. 27, 2020, now Pat. No. 11,464,943.

(60) Provisional application No. 62/934,370, filed on Nov. 12, 2019.

(51) Int. Cl.
*A61M 25/01* (2006.01)
*A61M 25/06* (2006.01)
*A61M 5/32* (2006.01)
*A61M 39/10* (2006.01)

(52) U.S. Cl.
CPC ...... *A61M 25/0113* (2013.01); *A61M 5/3293* (2013.01); *A61M 25/0606* (2013.01); *A61M 25/0618* (2013.01); *A61M 39/10* (2013.01); *A61M 2039/1077* (2013.01)

(58) Field of Classification Search
CPC ............ A61M 5/3275; A61M 25/0612; A61M 25/0618; A61M 25/0113; A61M 5/3293; A61M 25/0606; A61M 2039/1077; A61M 39/10
See application file for complete search history.

(56) References Cited

U.S. PATENT DOCUMENTS

| 2015/0018769 | A1* | 1/2015 | Farley | A61M 25/0606 604/164.08 |
|---|---|---|---|---|
| 2016/0361089 | A1 | 12/2016 | Farley et al. | |
| 2017/0274182 | A1 | 9/2017 | O'Bryan et al. | |
| 2018/0256885 | A1 | 9/2018 | Shevgoor et al. | |

FOREIGN PATENT DOCUMENTS

EP 3218031 A1 9/2017

* cited by examiner

*Primary Examiner* — Katherine H Schwiker
*Assistant Examiner* — Robert F Allen
(74) *Attorney, Agent, or Firm* — Kirton McConkie; Whitney Blair; Kevin Stinger

(57) ABSTRACT

A catheter assembly may include an introducer needle coupled to a needle hub, an intermediate member having a contact surface, a resilient member, and a ramp member. The resilient member may be coupled to one of the needle hub and the intermediate member. The ramp member may be coupled to the other one of the needle hub and the intermediate member. The resilient member may engage a ramp surface of the ramp member and impart a force on the intermediate member in a distal direction. The contact surface of the intermediate member may engage a proximal surface of a catheter adapter body and urge the catheter adapter body in the distal direction such that a catheter projecting from the catheter adapter body may be translated in the distal direction relative to the introducer needle.

9 Claims, 9 Drawing Sheets

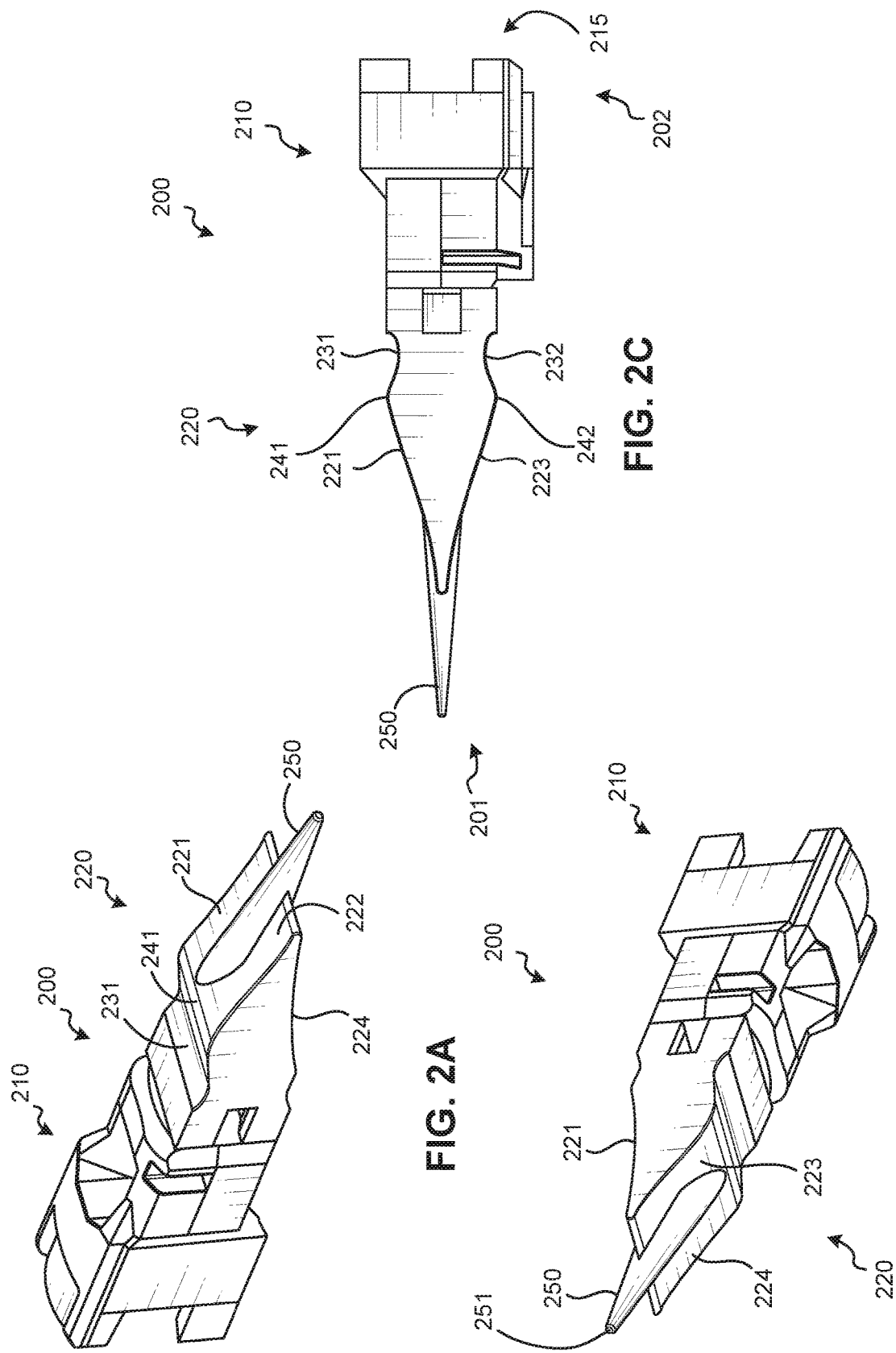

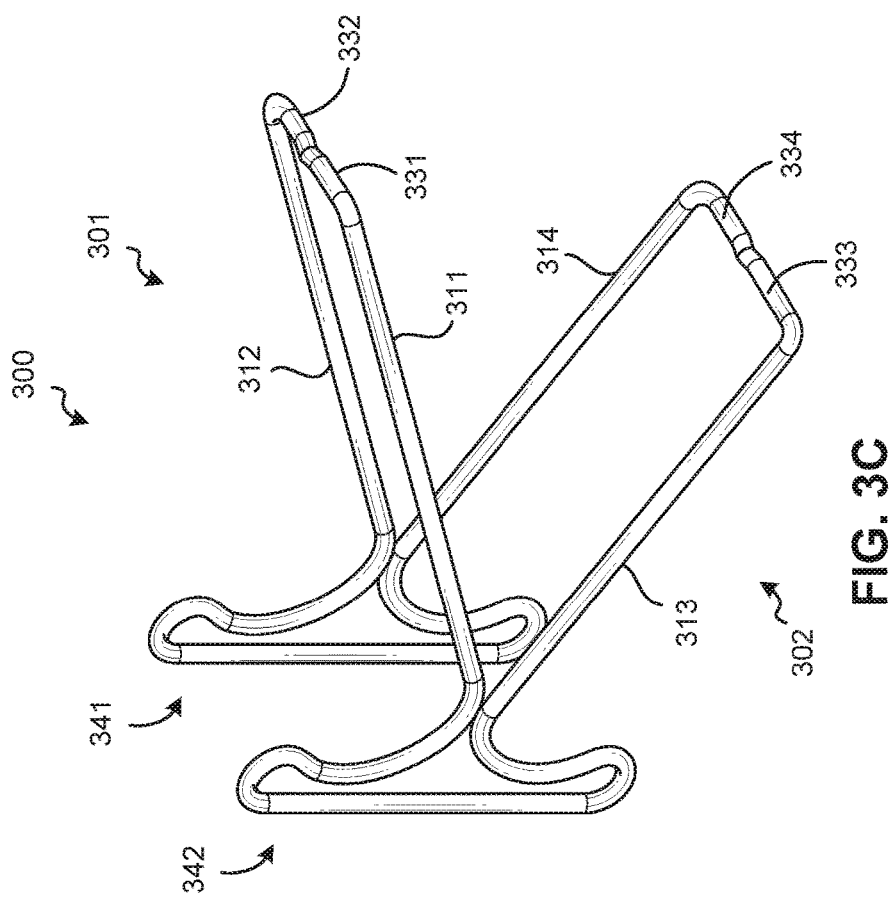
FIG. 3C
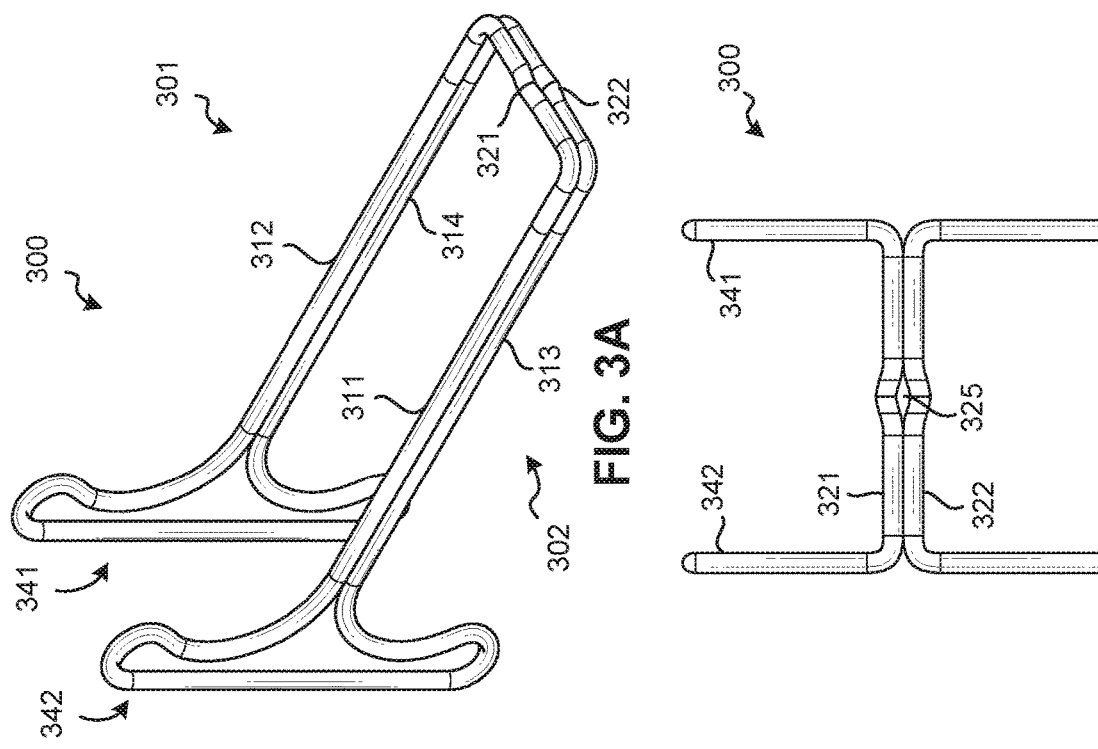
FIG. 3A
FIG. 3B

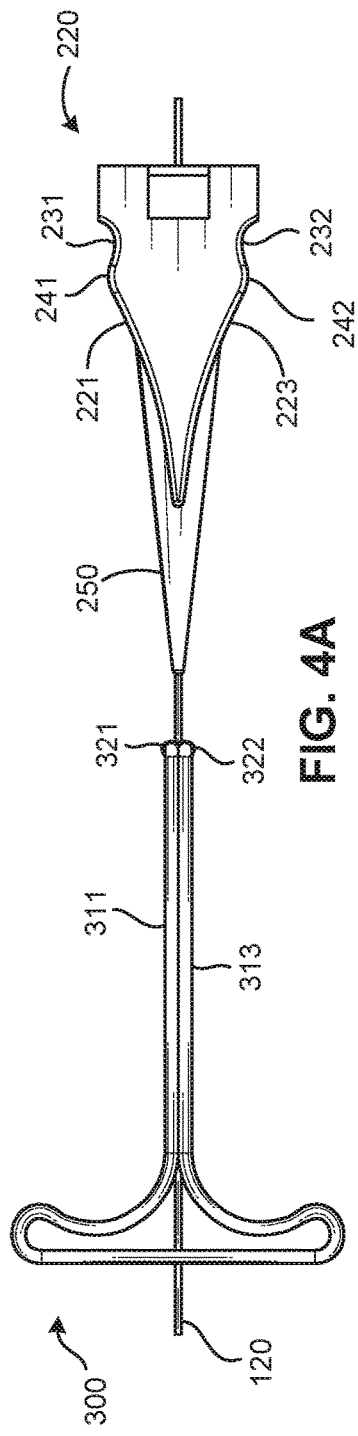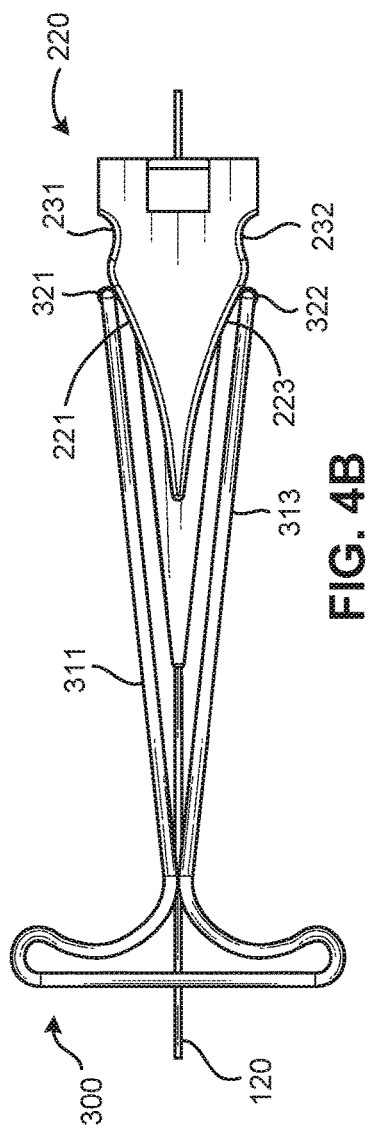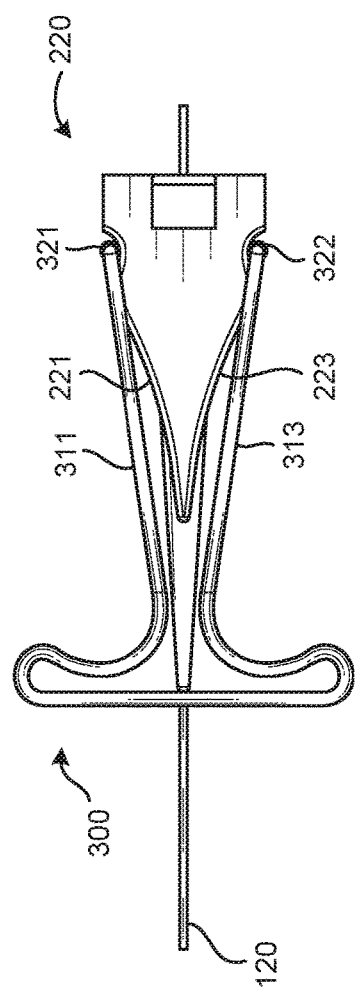

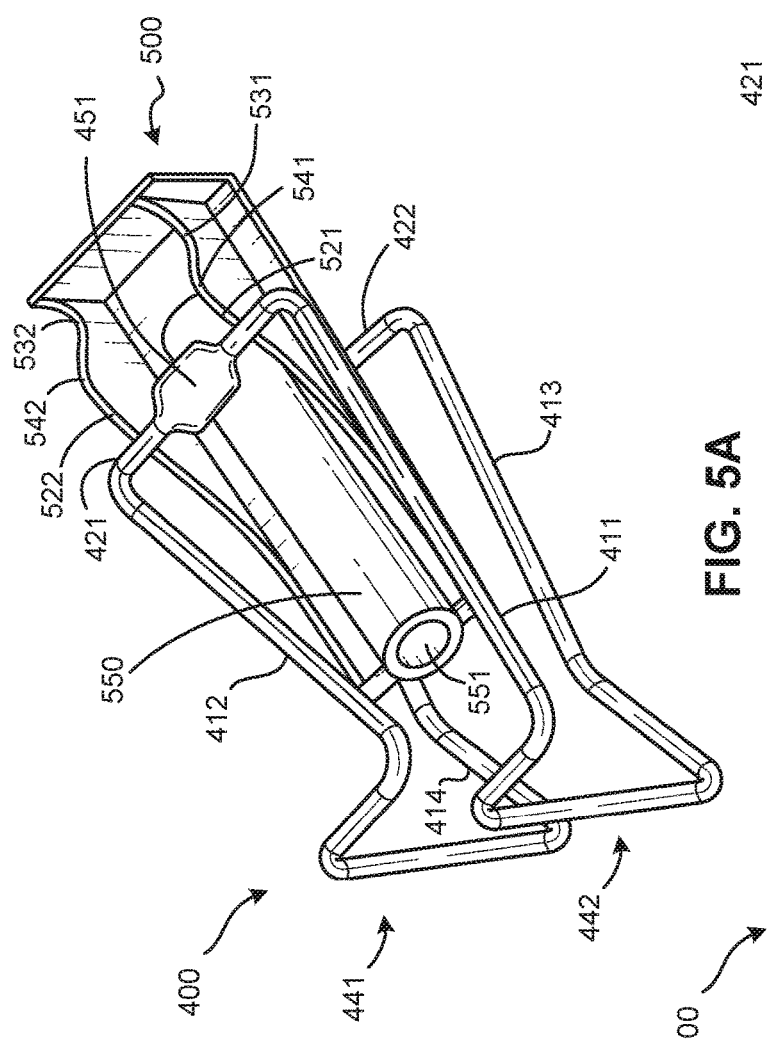
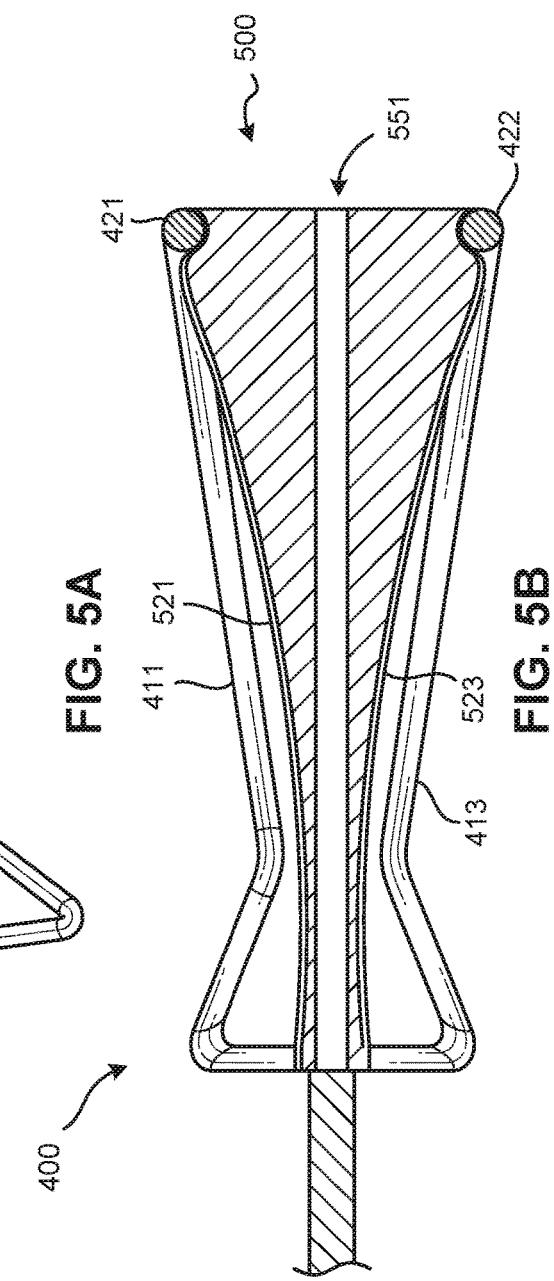
FIG. 5A
FIG. 5B

ASSISTED CATHETER ADVANCEMENT

RELATED APPLICATIONS

This application is a continuation of U.S. patent application Ser. No. 17/081,911, filed Oct. 27, 2020, and entitled ASSITED CATHETER ADVANCEMENT, which claims the benefit of U.S. Provisional Patent Application No. 62/934,370, filed Nov. 12, 2019, and entitled ASSISTED CATHETER ADVANCEMENT, which are incorporated herein in their entirety.

BACKGROUND

Catheters are commonly used for a variety of infusion therapies. For example, catheters may be used for infusing fluids into a patient such as saline solution, medication, total parenteral nutrition, etc. Catheters may also be used for withdrawing blood from the patient.

A common type of catheter is an over-the-needle peripheral intravenous catheter ("PIVC"). Other common types of catheters include, but are not limited to, peripherally inserted central catheters ("PICC"), central venous catheters ("CVC"), etc.

As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are typically inserted at a shallow angle through the skin and into a blood vessel of the patient, such as an artery, a vein, or any other vasculature of the patient. Once the PIVC has been properly placed within the blood vessel, the introducer needle may be withdrawn and the PIVC may be secured within the blood vessel by securing a catheter adapter (coupled with the PIVC) to the skin of the patient with dressing.

Some PIVC's can be associated with various additional components, such as valving components, needle safety components, etc., which may provide many additional useful features to clinicians. However, these additional components may also introduce undesirable characteristics to a PIVC system. For example, these additional components may lead to: (1) an increased overall length of a PIVC system, requiring a longer introducer needle; (2) new sources of friction transmitted to the introducer needle via the additional/longer components (e.g., the introducer needle may experience higher early stage drag forces as the introducer needle is withdrawn/advanced through the additional/longer components. This may interfere with a clinician's tactile sensation and ability to properly place and maintain a catheter within a patient's vein); and (3) an increased length of the introducer needle that is unsupported by other components of the PIVC system as the introducer needle is withdrawn from the other components of the PIVC system. This longer "unsupported portion" of the introducer needle may result in increased flexion that can allow other parts of the PIVC system to "wobble" back and forth in a flimsy manner and may result in dislodgment of the catheter from the vein. Accordingly, improved catheter assemblies, systems, and methods would be desirable.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to catheter assemblies, systems, and methods. The various catheter assemblies, systems, and methods of the present disclosure have been developed in response to the present state of the art, and in particular, in response to the problems and needs in the art that have not yet been fully solved by currently available catheter assemblies, systems, and methods for inserting a catheter into a blood vessel of a patient.

In some embodiments, a catheter system may include a needle assembly, a driving spring, and a needle-safety shield. The needle assembly may include an introducer needle and a needle hub coupled to the introducer needle. The driving spring may be coupled to the needle hub. The driving spring may include a superior portion having a first spring arm, a second spring arm, and a first cross-member coupling the first spring arm to the second spring arm. The driving spring may also include an inferior portion having a third spring arm, a fourth spring arm, and a second cross-member coupling the third spring arm to the fourth spring arm. The driving spring may further include a first resilient portion and a second resilient portion. The first resilient portion may couple the first spring arm to the third spring arm and the second resilient portion may couple the second spring arm to the fourth spring arm. The first and second resilient portions may also apply a bias force to the first and second cross-members to urge the first and second cross-members toward each other. The needle-safety shield may include a contact surface disposed at a distal end of the needle-safety shield, and the needle-safety shield may be configured to slidably receive the introducer needle therein. The needle-safety shield may also include a ramp member disposed at a proximal end of the needle-safety shield. The ramp member may include a first ramp surface configured to receive a first guide surface of the first cross-member, a second ramp surface configured to receive a second guide surface of the first cross-member, a third ramp surface configured to receive a third guide surface of the second cross-member, and a fourth ramp surface configured to receive a fourth guide surface of the second cross-member. The driving spring may be configured to engage the ramp member and impart a force on the needle-safety shield to urge the needle-safety shield in a distal direction relative to the needle hub. The contact surface of the needle-safety shield may engage a proximal surface of a catheter adapter body and urge the catheter adapter body in the distal direction relative to the needle hub and a catheter projecting from a distal end of the catheter adapter body may be translated in the distal direction relative to the introducer needle.

In some embodiments of the catheter system, the first and second cross-members may be configured to grasp the introducer needle between the first and second cross-members as the first and second cross-members are urged together.

In some embodiments of the catheter system, the first ramp surface may include a first concave surface portion, the second ramp surface may include a second concave surface portion, the third ramp surface may include a third concave surface portion, and the fourth ramp surface may include a fourth concave surface portion.

In some embodiments of the catheter system, the first concave surface portion may include a first radius, the second concave surface portion may include a second radius, the third concave surface portion may include a third radius, and the fourth ramp surface may include a fourth radius.

In some embodiments of the catheter system, the first radius, the second radius, the third radius, and the fourth radius may be substantially equal to each other.

In some embodiments of the catheter system, the ramp member may include at least one plateau portion.

In some embodiments of the catheter system, the ramp member may include at least one stop bump adjacent to the at least one plateau portion.

In some embodiments, a catheter assembly may include an introducer needle coupled to a needle hub, an intermediate member, a resilient member, and a ramp member. The intermediate member may include a contact surface disposed at a distal end of the intermediate member. The intermediate member may be configured to slidably receive the introducer needle therethrough. The resilient member may be coupled to one of the needle hub and the intermediate member. The ramp member may be coupled to the other one of the needle hub and the intermediate member. The resilient member may be configured to engage at least one ramp surface of the ramp member and impart a force on the intermediate member to urge the intermediate member in a distal direction relative to the needle hub. The contact surface of the intermediate member may engage a proximal surface of a catheter adapter body and urge the catheter adapter body in the distal direction relative to the needle hub and a catheter projecting from a distal end of the catheter adapter body may be translated in the distal direction relative to the introducer needle.

In some embodiments of the catheter assembly, the resilient member may include a driving spring. The driving spring may include a superior portion having a first spring arm, a second spring arm, and a first cross-member coupling the first spring arm to the second spring arm. The driving spring may also include an inferior portion having a third spring arm, a fourth spring arm, and a second cross-member coupling the third spring arm to the fourth spring arm. The driving spring may also include a first resilient portion and a second resilient portion. The first resilient portion may couple the first spring arm to the third spring arm, the second resilient portion may couple the second spring arm to the fourth spring arm, and the first and second resilient portions may apply a bias force to the first and second cross-members to urge the first and second cross-members toward each other. In some embodiments, the catheter system may include more than two resilient portions and/or more than four ramp surfaces.

In some embodiments of the catheter assembly, the first and second cross-members may be configured to grasp the introducer needle between the first and second cross-members as the first and second cross-members are urged together.

In some embodiments of the catheter assembly, the at least one ramp surface of the ramp member may include a first ramp surface configured to receive a first guide surface of the first cross-member, a second ramp surface configured to receive a second guide surface of the first cross-member, a third ramp surface configured to receive a third guide surface of the second cross-member, and a fourth ramp surface configured to receive a fourth guide surface of the second cross-member.

In some embodiments of the catheter assembly, the at least one ramp surface may include a concave surface portion having a first radius.

In some embodiments of the catheter assembly, the at least one ramp surface may include a plateau portion.

In some embodiments of the catheter assembly, the at least one ramp surface may include a stop bump intermediate the concave surface portion and the plateau portion.

In some embodiments, a method of inserting a catheter into a blood vessel of a patient may be facilitated through use of a catheter assembly that may include an introducer needle coupled to a needle hub, an intermediate member having a contact surface disposed at a distal end of the intermediate member, a resilient member coupled to one of the needle hub and the intermediate member, and a ramp member coupled to the other one of the needle hub and the intermediate member. The method may include inserting a distal end of the introducer needle within a blood vessel of the patient, and advancing the intermediate member proximally relative to the introducer needle, thereby: (1) engaging the resilient member with a ramp surface of the ramp member to impart a force on the intermediate member and urge the intermediate member in a distal direction relative to the needle hub; (2) engaging the contact surface of the intermediate member with a proximal surface of a catheter adapter body to urge the catheter adapter body in the distal direction relative to the needle hub; and (3) urging the catheter coupled to the catheter adapter body in the distal direction relative to the introducer needle until a distal end of the catheter is inserted within the blood vessel.

In some embodiments of the method, the method may further include moving the needle hub and the introducer needle in a proximal direction relative to the catheter, and withdrawing the introducer needle from the catheter.

In some embodiments of the method, the resilient member may include a driving spring. The driving spring may include a superior portion having a first spring arm, a second spring arm, and a first cross-member coupling the first spring arm to the second spring arm. The driving spring may also include an inferior portion having a third spring arm, a fourth spring arm, and a second cross-member coupling the third spring arm to the fourth spring arm. The driving spring may further include a first resilient portion and a second resilient portion. The first resilient portion may couple the first spring arm to the third spring arm, the second resilient portion may couple the second spring arm to the fourth spring arm, and the first and second resilient portions may apply a bias force to the first and second cross-members to urge the first and second cross-members toward each other.

In some embodiments of the method, the first and second cross-members may be configured to grasp the introducer needle between the first and second cross-members as the first and second cross-members are urged toward each other. The method may further include grasping the introducer needle between the first and second cross-members of the driving spring as the introducer needle is at least partially withdrawn from the catheter.

In some embodiments of the method, the ramp surface may include a first ramp surface configured to receive a first guide surface of the first cross-member, a second ramp surface configured to receive a second guide surface of the first cross-member, a third ramp surface configured to receive a third guide surface of the second cross-member, and a fourth ramp surface configured to receive a fourth guide surface of the second cross-member. The method may further include: (1) engaging the first guide surface with the first ramp surface and imparting a first force that urges the intermediate member in the distal direction relative to the needle hub; (2) engaging the second guide surface with the second ramp surface and imparting a second force that urges the intermediate member in the distal direction relative to the needle hub; (3) engaging the third guide surface with the third ramp surface and imparting a third force that urges the intermediate member in the distal direction relative to the needle hub; and (4) engaging the fourth guide surface with the fourth ramp surface and imparting a fourth force that urges the intermediate member in the distal direction relative to the needle hub.

In some embodiments of the method, the ramp surface may include a concave surface portion having a first radius. The method may further include engaging the resilient member with the concave surface portion to impart the force on the intermediate member and urge the intermediate member in the distal direction relative to the needle hub.

It is to be understood that both the foregoing general description and the following detailed description are exemplary and explanatory and are not restrictive of the embodiments of the present disclosure, as claimed. It should be understood that the various embodiments of the present disclosure are not limited to the arrangements and instrumentality shown in the drawings. It should also be understood that the embodiments of the present disclosure may be combined, or that other embodiments may be utilized and that structural changes, unless so claimed, may be made without departing from the spirit or scope of the various embodiments of the present disclosure. The following detailed description is, therefore, not to be taken in a limiting sense.

BRIEF DESCRIPTION OF THE DRAWINGS

Example embodiments will be described and explained with additional specificity and detail through the use of the accompanying drawings in which:

FIG. 2A is a perspective top view of a needle-safety shield, according to some embodiments;

FIG. 2B is a perspective bottom view of the needle-safety shield of FIG. 2A;

FIG. 2C is a side view of the needle-safety shield of FIG. 2A;

FIG. 3A is a perspective top view of a driving spring, according to some embodiments;

FIG. 3B is a front view of the driving spring of FIG. 3A;

FIG. 3C is a perspective top view of the driving spring of FIG. 3A, showing the distal ends of the driving spring pulled apart;

FIGS. 4A-4C illustrate various side views of the driving spring of FIG. 3A as it is loaded onto a ramp member of the needle-safety shield of FIG. 2A; FIG. 4A is a side view of the driving spring before it is loaded onto the ramp member; FIG. 4B is a side view of the driving spring sliding up the ramp member; and FIG. 4C is a side view of the driving spring when it is fully loaded onto the ramp member;

FIG. 5A is a perspective top view of a driving spring being loaded onto a ramp member, according to some alternative embodiments;

FIG. 5B is a cross-sectional side view of the driving spring fully loaded onto the ramp member of FIG. 5A;

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1A:
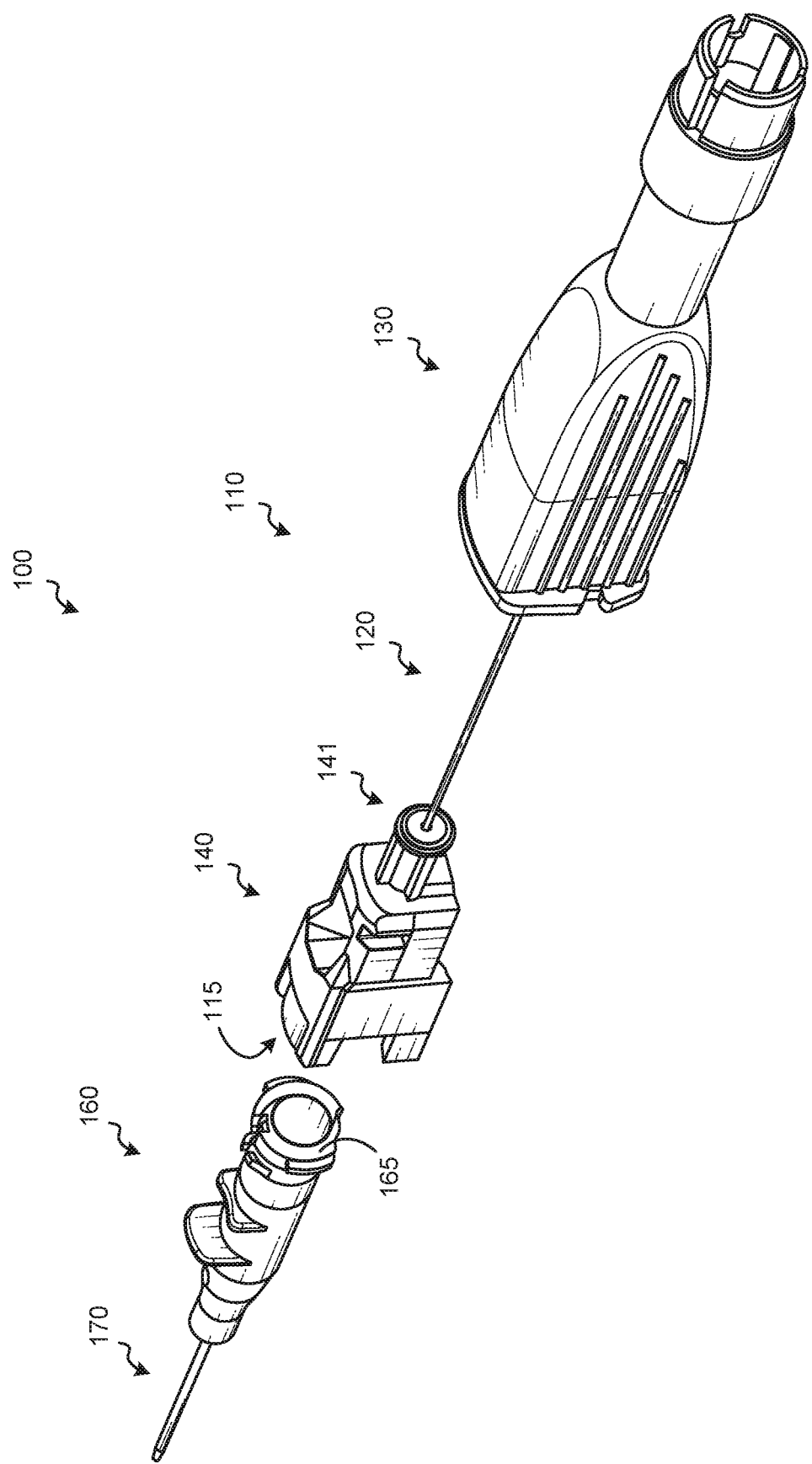
FIG. 1A is an exploded view of an example catheter system, according to some embodiments.
Figure 1B:
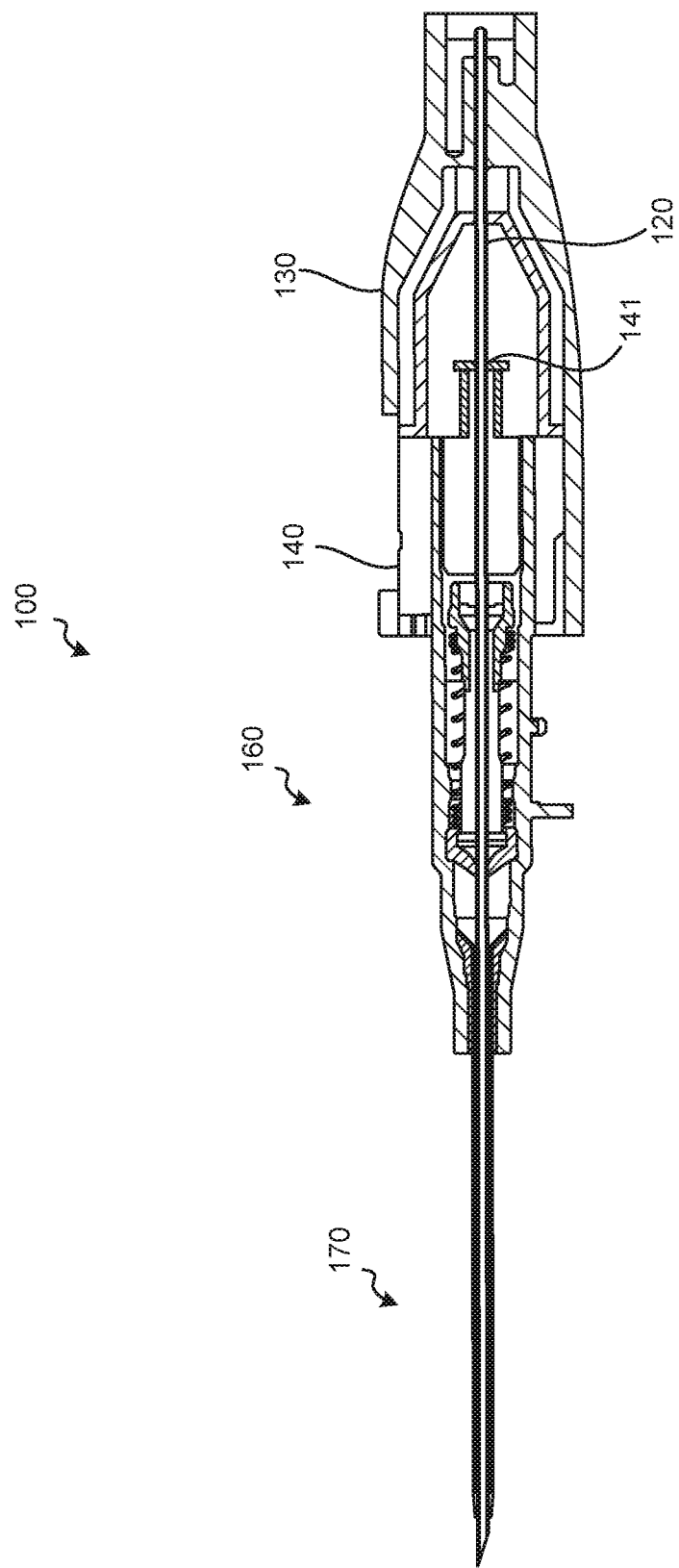
FIG. 1B is a cross-sectional side view of the example catheter system of FIG. 1A, after assembly.

FIGS. 1A and 1B illustrate various views of an example catheter system 100 (or catheter assembly) that may be utilized with the teachings of the present disclosure, according to some embodiments. Specifically, FIG. 1A is an exploded view of the example catheter system 100 and FIG. 1B is a cross-sectional side view of the example catheter system 100, after the example catheter system 100 has been assembled.

The catheter system 100 may generally include a needle assembly 110, a needle-safety shield 140, a catheter adapter body 160, and a catheter 170 coupled to and projecting from a distal end of the catheter adapter body 160. The needle assembly 110 may include an introducer needle 120 coupled to a needle hub 130. The needle-safety shield 140 may include a septum 141 configured to slidably receive the introducer needle 120 therethrough, and a contact surface 115 disposed at a distal end of the needle-safety shield 140. The catheter adapter body 160 may include a proximal surface 165 configured to engage the contact surface 115 of the needle-safety shield 140, as will be explained below in more detail with respect to FIGS. 2A-8.

FIGS. 2A-2C illustrate various views of a needle-safety shield 200 (or intermediate member), according to some embodiments. The needle-safety shield 200 may be utilized in conjunction with the example catheter system 100 of FIGS. 1A and 1B, or with any other suitable catheter system known or contemplated in the art. The needle-safety shield 200 may generally include a needle-safety shield portion 210 disposed at a distal end 202 of the needle-safety shield 200, and a ramp member portion (or ramp member 220) disposed at a proximal end 201 of the needle-safety shield 200.

The needle-safety shield portion 210 may include a contact surface 215 at a distal end of the needle-safety shield portion 210. The needle-safety shield portion 210 may be configured to internally trap a distal end of the introducer needle 120 to protect a clinician against accidental exposure to the sharp distal end of the introducer needle 120. The needle-safety shield portion 210 (and/or the ramp member 220) may further include one or more internal septa (not shown), which may be configured to facilitate the proper valving of fluids in a catheter system that utilizes the modified needle-safety shield 200 shown in FIGS. 2A-2C.

In at least some embodiments, the ramp member 220 may be integrally formed with the needle-safety shield portion 210. For example, the ramp member 220 may be integrally formed with the needle-safety shield portion 210 via an injection molding process. However, it will also be understood that in other embodiments, the ramp member 220 may not be integrally formed with the needle-safety shield portion 210. For example, the ramp member 220 and the needle-safety shield portion 210 may be separately formed and then coupled together via an adhesive process, or not coupled together at all. Moreover, in some catheter system embodiments, the ramp member 220 may be utilized without the needle-safety shield portion 210 to form a simple intermediate member. In yet further embodiments, the ramp member 220 may be combined with any number of different components in order to form any number of different intermediate members that incorporate the ramp member 220.

In general, the ramp member 220 may include a first ramp surface 221, a second ramp surface 222, a third ramp surface 223, a fourth ramp surface 224, a first plateau portion 231, a second plateau portion 232, a first stop bump 241, a second stop bump 242, and a ramp projection 250 having ramp needle aperture 251 formed therethrough.

Each ramp surface may be angled relative to an introducer needle 120 that may pass through the ramp needle aperture 251. A magnitude or steepness of an angle associated with a given ramp surface will generally determine a magnitude of a distally directed force that may be generated by a driving spring pressing against the ramp surface, as will be discussed in more detail below.

In some embodiments, each ramp surface may also include a surface portion that includes a concave shape. For example, the first ramp surface 221 may include a first concave surface portion, the second ramp surface 222 may include a second concave surface portion, the third ramp surface 223 may include a third concave surface portion, and the fourth ramp surface 224 may include a fourth concave surface portion. Moreover, each concave surface portion may have a radius that is associated with each concave surface portion. For example, the first concave surface portion may have a first radius, the second concave surface portion may have a second radius, the third concave surface portion may have a third radius, and the fourth ramp surface may have a fourth radius. In at least one embodiment, each of the first radius, the second radius, the third radius, and the fourth radius may be substantially equal to each other. However, it will also be understood that in other embodiments the first radius, the second radius, the third radius, and/or the fourth radius may be similar and/or different from each other in any combination.

A magnitude of a radius associated with a concave ramp surface will generally determine a maximum force and a minimum force that may be generated by a driving spring pressing against the concave ramp surface (which will be discussed in more detail below). The radius of the concave ramp surface will also determine transitional force characteristics that are imparted to an introducer needle as the driving springs moves along the concave ramp surface between the top of the concave ramp surface (maximum force) toward the bottom of the concave ramp surface (minimum force). For example, a concave ramp surface may be designed with a radius that substantially normalizes early stage drag forces that are experienced by an introducer needle (e.g., when a clinician first begins withdrawing the introducer needle from a catheter system), by applying an appropriate maximum force to the introducer needle early during withdrawal. However, as the clinician continues to withdraw the introducer needle from the catheter system, the drag forces experienced by the introducer needle will typically decrease. Accordingly, the radius of the concave ramp surface also helps the introducer needle maintain a normalized drag force profile on the introducer needle as it is withdrawn from the catheter system by continuously reducing the force applied to the introducer needle as the driving spring moves along the concave ramp surface and transitions between the maximum force (e.g., when the driving spring is at the top of the concave ramp surface) toward the minimum force (e.g., when the driving spring is at the bottom of the concave ramp surface).

In some embodiments, the first stop bump 241 may be located adjacent to and/or intermediate the first and second ramp surfaces 221, 222 and the first plateau portion 231, and the second stop bump 242 may be located adjacent to and/or intermediate the third and fourth ramp surfaces 223, 224 and the second plateau portion 232. The shape of the first and second plateau portions 231, 232 and the first and second stop bumps 241, 242 may help to bias a driving spring to keep it in place on top of the ramp member 220 (e.g., fully loaded onto the ramp member 220) until a clinician is ready to withdraw the introducer needle from the catheter system.

The ramp projection 250 may also help reduce flexion and "wobble" in an introducer needle passing through the ramp needle aperture 251. The ramp projection 250 may accomplish this by decreasing a length of the introducer needle that is unsupported by other components of the catheter system when the introducer needle is at least partially withdrawn from the catheter system.

FIGS. 3A-3C illustrate various views of a resilient member or driving spring 300, according to some embodiments. Specifically, FIG. 3A is a perspective top view of the driving spring 300, FIG. 3B is a front view of the driving spring 300, and FIG. 3C is a perspective top view of the driving spring 300, shown pulled apart. In general, the driving spring 300 includes a superior portion 301, an inferior portion 302, a first resilient portion 341, and a second resilient portion 342.

The superior portion 301 may include a first spring arm 311, a second spring arm 312, and a first cross-member 321 that couples the first spring arm 311 to the second spring arm 312. Likewise, the inferior portion 302 may include a third spring arm 313, a fourth spring arm 314, and a second cross-member 322 that couples the third spring arm 313 to the fourth spring arm 314. The second resilient portion 342 may couple the first spring arm 311 to the third spring arm 313 and the first resilient portion 341 may couple the second spring arm 312 to the fourth spring arm 314. The first and second resilient portions 341, 342 may each apply one or more bias forces to the first and second cross-members 321, 322 to urge the first and second cross-members 321, 322 toward each other. In at least some embodiments, the first and second cross-members 321, 322 may be configured to grasp an introducer needle between the first and second cross-members 321, 322 when the first and second cross-members 321, 322 are urged together. For example, a spring needle aperture 325 may be formed between the first and second cross-members 321, 322, as shown in FIG. 3B. The spring needle aperture 325 may be sized to receive and/or grasp an introducer needle between the first and second cross-members 321, 322 when the first and second cross-members 321, 322 are urged toward each other by the first and second resilient portions 341, 342.

In at least some embodiments, the first cross-member 321 may include a first guide surface 331 and a second guide surface 332. The second cross-member 322 may include a third guide surface 333 and a fourth guide surface 334. In these embodiments, the first ramp surface 221 may be configured to receive the first guide surface 331 of the first cross-member 321, the second ramp surface 222 may be configured to receive the second guide surface 332 of the first cross-member 321, the third ramp surface 223 may be configured to receive the third guide surface 333 of the second cross-member 322, and the fourth ramp surface 224 may be configured to receive the fourth guide surface 334 of the second cross-member 322. In this manner, the driving spring 300 may be configured to engage the ramp member 220 (once it has been loaded onto the ramp member 220) and impart a force on the needle-safety shield 200 to urge the needle-safety shield 200 in a distal direction relative to the needle hub 130. This will then cause the contact surface 215 of the needle-safety shield 200 to engage the proximal surface 165 of a catheter adapter body 160 and urge the catheter adapter body 160 in the distal direction relative to the needle hub 130. This, in turn, will urge the catheter 170 in the distal direction relative to the introducer needle 120. In this manner, the drag forces experienced by the introducer needle 120 may be reduced and/or normalized in order to provide a uniform operation/feel to the clinician that can help the clinician better guide the catheter 170 and advance or place the catheter 170 within a blood vessel of a patient.

FIGS. 4A-4C illustrate various side views of the driving spring 300 as it is loaded onto the ramp member 220. FIG. 4A shows the driving spring 300 before it is loaded onto the ramp member 220. FIG. 4A also shows how the introducer needle 120 can be grasped between the first and second cross-members 321, 322. In this manner, there is only a short length of the introducer needle 120 that is "unsupported" between the first and second cross-members 321, 322 and the tip of the ramp projection 250. This design results in reduced flexion and wobble that is experienced by the introducer needle 120. FIG. 4B shows the driving spring 300 sliding up the ramp member 220 as it is loaded onto the ramp member 220, and FIG. 4C shows the driving spring 300 after it has been fully loaded onto the ramp member 220. FIG. 4C also shows how the first and second cross-members 321, 322 respectively fit within the first and second plateau portions 231, 232 of the ramp member 220 to maintain the driving spring 300 fully loaded onto the ramp member 220.

Figure 6:
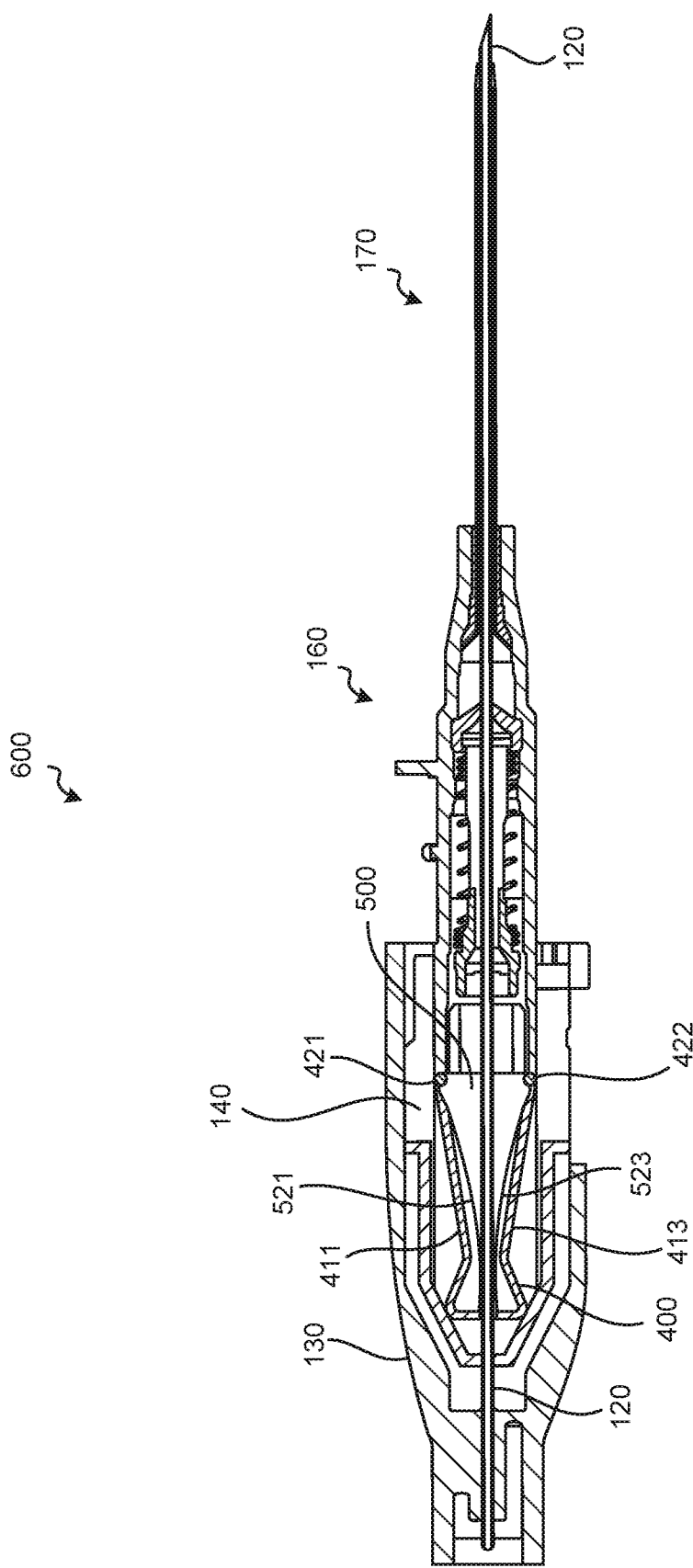
FIG. 6 is a cross-sectional side view of an example catheter system incorporating the driving spring and ramp member of FIG. 5A.

FIGS. 5A-6 illustrate various views of a resilient member or driving spring 400 and an intermediate or ramp member 500, according to alternative embodiments of the present disclosure. Specifically, FIG. 5A is a perspective top view of the driving spring 400 as it is loaded onto the ramp member 500; FIG. 5B is a cross-sectional side view of the driving spring 400 after it has been fully loaded onto the ramp member 500; and FIG. 6 is a cross-sectional side view of an example catheter assembly or catheter system 600 incorporating the driving spring 400 and ramp member 500 of FIGS. 5A and 5B.

The ramp member 500 may include a first ramp surface 521, a second ramp surface 522, a third ramp surface 523, a fourth ramp surface (not visible in FIGS. 5A-6), a first plateau portion 531, a second plateau portion 532, a first stop bump 541, a second stop bump 542, and a ramp projection 550 having ramp needle aperture 551 formed therethrough. The driving spring 400 may include a first spring arm 411, a second spring arm 412, and a first cross-member 421 that couples the first spring arm 411 to the second spring arm 412. The driving spring 400 may also include a third spring arm 413, a fourth spring arm 414, and a second cross-member 422 that couples the third spring arm 413 to the fourth spring arm 414. A second resilient portion 442 may couple the first spring arm 411 to the third spring arm 413 and a first resilient portion 441 may couple the second spring arm 412 to the fourth spring arm 414. The first and second resilient portions 441, 442 may each apply one or more bias forces to the first and second cross-members 421, 422 to urge the first and second cross-members 421, 422 toward each other. In at least some embodiments, the first and second cross-members 421, 422 may be configured to grasp an introducer needle between the first and second cross-members 421, 422 when the first and second cross-members 421, 422 are urged together. For example, a first spring plate 451 and a second spring plate (not visible in FIGS. 5A-6) may be formed in the first and second cross-members 421, 422 and shaped to receive and/or grasp an introducer needle between the first and second cross-members 421, 422 when the first and second cross-members 421, 422 are urged toward each other by the first and second resilient portions 441, 442.

As shown in FIG. 6, the driving spring 400 may be coupled to the needle hub 130, and the ramp member 500 may be coupled to the needle-safety shield 140. However, it will also be understood that the driving spring 400 may be coupled to the needle-safety shield 140 and the ramp member 500 may be coupled to the needle hub 130, in at least some embodiments. The driving spring 400 may be configured to engage the ramp member 500 and impart a force on the needle-safety shield 140 to urge the needle-safety shield 140 in a distal direction relative to the needle hub 130. This will then cause a contact surface of the needle-safety shield 140 to engage a proximal surface of a catheter adapter body 160 and urge the catheter adapter body 160 in the distal direction relative to the needle hub 130. This, in turn, will urge the catheter 170 in the distal direction relative to the introducer needle 120. In this manner, drag forces experienced by the introducer needle 120 from other components of the catheter system 600 may be reduced and/or normalized in order to provide a uniform operation and "feel" to the clinician, which can help the clinician better guide the catheter 170 and place the catheter 170 within a blood vessel of a patient.

Figure 7:
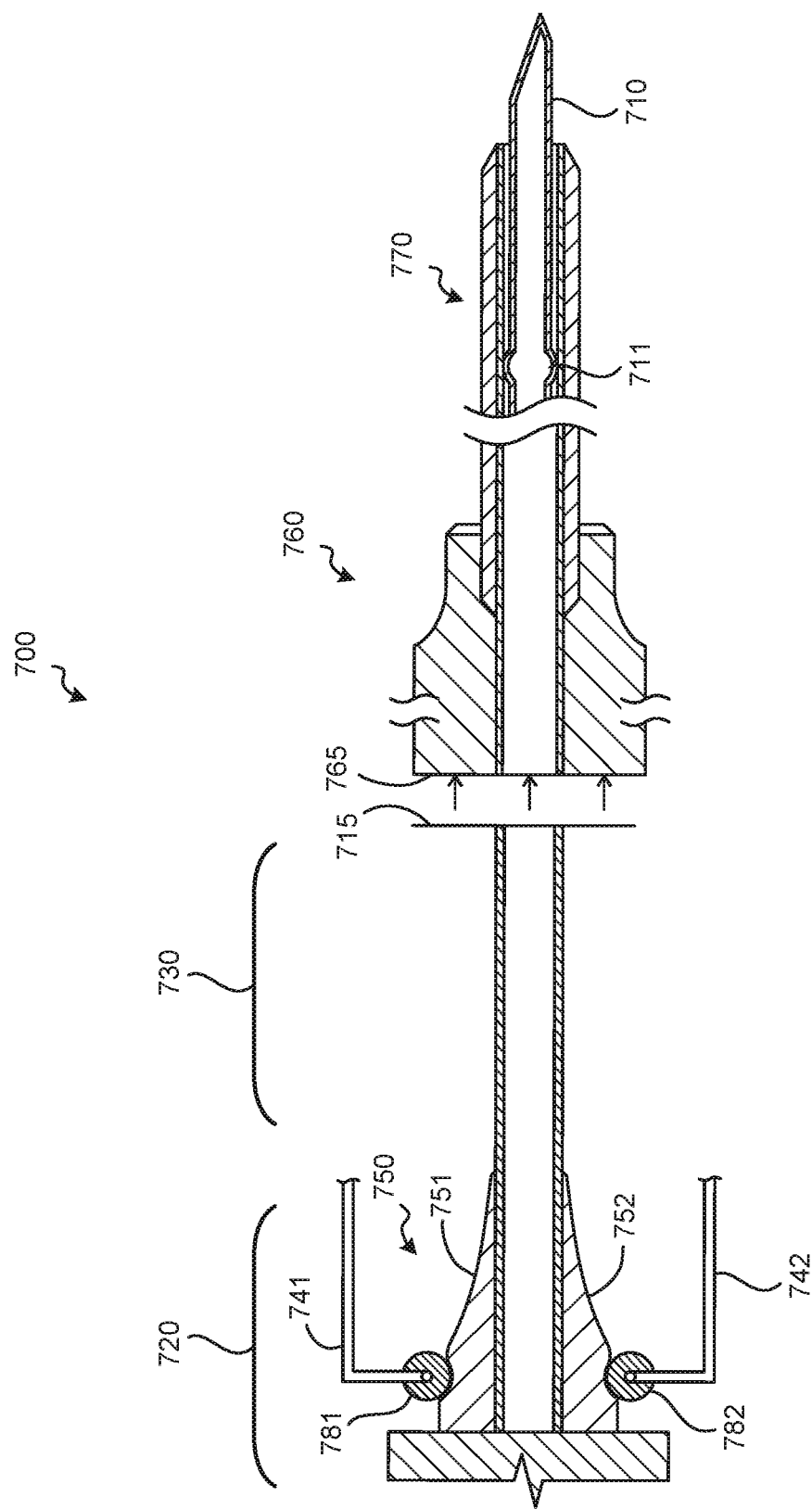
FIG. 7 is a partial cross-sectional side view of an example catheter system, according to some alternative embodiments.

FIG. 7 illustrates a partial cross-sectional side view of an example catheter assembly or catheter system 700, according to an alternative embodiment of the present disclosure. In general, the catheter system 700 may include an introducer needle 710 comprising a needle bump 711, a needle hub 720 coupled to the introducer needle 710, an intermediate member 730 comprising a contact surface 715, a first resilient member 741, a first bearing member 781 coupled to the first resilient member 741, a second resilient member 742, a second bearing member 782 coupled to the second resilient member 742, a ramp member 750 comprising a first ramp surface 751 and a second ramp surface 752, a catheter adapter body 760 comprising a proximal surface 765, and a catheter 770 extending from a distal end of the catheter adapter body 760.

The catheter system 700 may function in a similar manner to other catheter systems described herein. However, in at least some embodiments the first and second bearing members 781, 782 may be configured to rotate relative to the first and second resilient members, respectively. In this manner, friction between the first resilient member 741 and the first ramp surface 751 may be reduced, and friction between the second resilient member 742 and the second ramp surface 752 may also be reduced. Moreover, the first and second resilient members 741, 742 may be coupled to the intermediate member 730, and the ramp member 750 may be coupled to the needle hub 720, as opposed to other catheter system embodiments disclosed herein. In this manner, the first and second resilient members 741, 742 may engage the first and second ramp surfaces 751, 752 to impart a force on the intermediate member 730 and urge the intermediate member 730 in a distal direction relative to the needle hub 720. This may cause the contact surface 715 of the intermediate member 730 to engage the proximal surface 765 of the catheter adapter body 760 and urge the catheter adapter body 760 in the distal direction relative to the needle hub 720. This, in turn, may urge the catheter 770 in the distal direction relative to the introducer needle 710. In this manner, drag forces experienced by the introducer needle 710 (from other components in the catheter system 700) may be reduced and/or normalized in order to provide a uniform drag force to the clinician to help the clinician guide the catheter 770 into a blood vessel of a patient.

Figure 8:
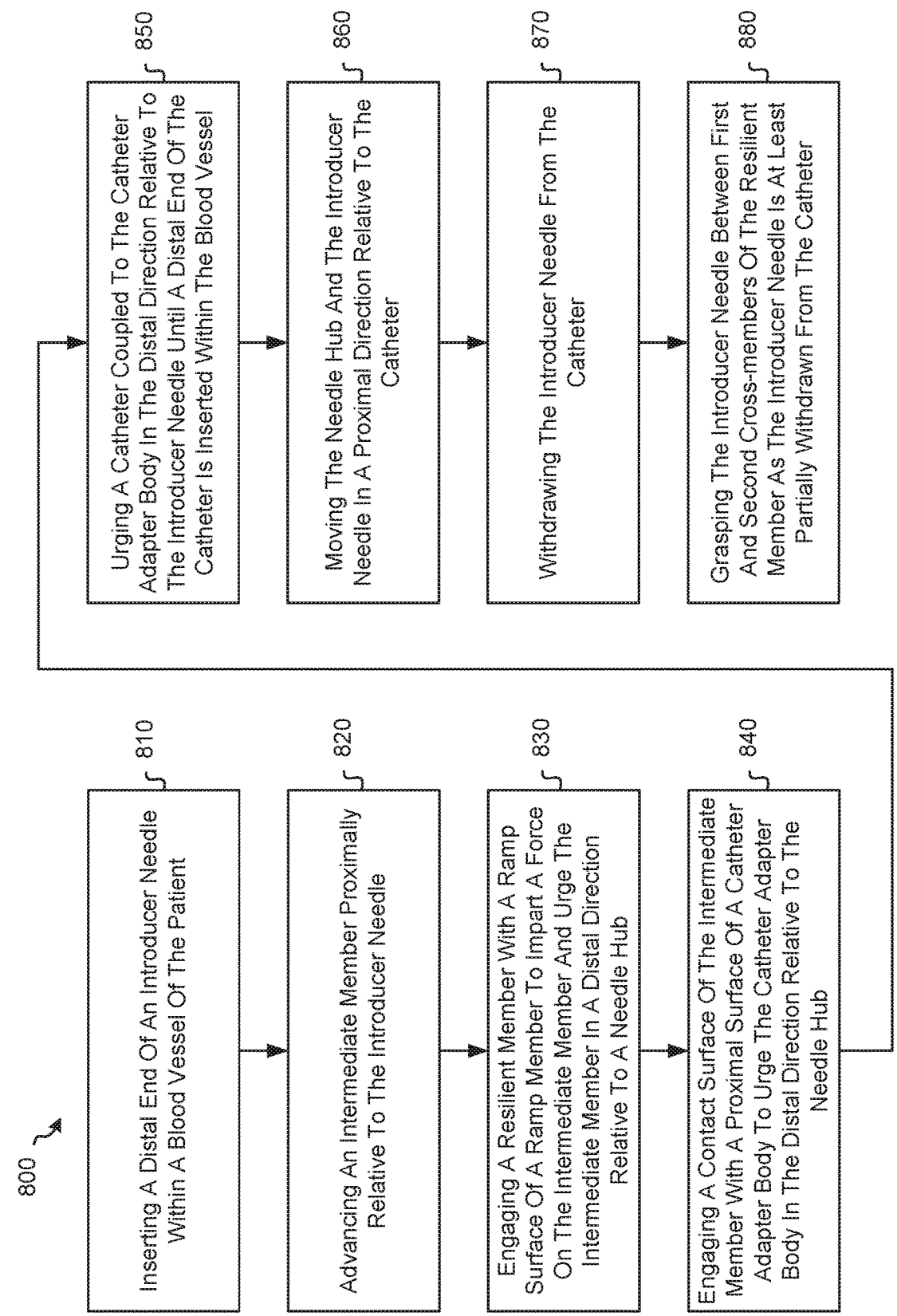
FIG. 8 is a flow chart of a method for inserting a catheter into a blood vessel of a patient.

FIG. 8 is a flow chart of a method 800 for inserting a catheter into a blood vessel of a patient, according to some embodiments of the present disclosure. The method 800 may be facilitated through use of a catheter assembly or catheter system comprising an introducer needle coupled to a needle hub, an intermediate member having a contact surface disposed at a distal end of the intermediate member, a resilient member coupled to one of the needle hub and the intermediate member, and a ramp member coupled to the other one of the needle hub and the intermediate member.

The method 800 may begin with a step 810 in which a distal end of the introducer needle may be inserted into a blood vessel of a patient by a clinician.

Once the clinician has inserted the distal end of the introducer needle into the blood vessel of the patient, the method 800 may proceed to a step 820 in which the clinician may advance the intermediate member proximally relative to the introducer needle.

Once the clinician has advanced the intermediate member proximally relative to the introducer needle, the method 800 may proceed to a step 830 in which the resilient member may be engaged with a ramp surface of the ramp member to impart a force on the intermediate member and urge the intermediate member in a distal direction relative to the needle hub.

Once the resilient member has been engaged with the ramp surface and a force has been imparted on the intermediate member to urge the intermediate member in the distal direction relative to the needle hub, the method 800 may proceed to a step 840 in which a contact surface of the intermediate member may be engaged with a proximal surface of a catheter adapter body to urge the catheter adapter body in the distal direction relative to the needle hub.

Once the catheter adapter body has been urged in the distal direction relative to the needle hub, the method 800 may proceed to a step 850 in which the catheter coupled to the catheter adapter body may be urged in the distal direction relative to the introducer needle. In some embodiments, the catheter coupled to the catheter adapter body may be urged in the distal direction relative to the introducer needle in order to insert a distal end of the catheter into the blood vessel or further advance the introducer needle within the blood vessel.

Alternatively, or in addition thereto, the method 800 may also proceed to any one or more of steps 860, 870, and/or 880. For example, once the catheter has been urged in the distal direction relative to the introducer needle, the method 800 may proceed to the step 860 and/or the step 870 in which the needle hub and the introducer needle may be moved in a proximal direction relative to the catheter and the introducer needle may be fully, or at least partially, withdrawn from the catheter. Once the introducer needle has been at least partially withdrawn from the catheter, the method 800 may further proceed to the step 880 in which the introducer needle may be grasped between first and second cross-members of the resilient member as the introducer needle is at least partially withdrawn from the catheter, and the method 800 may end.

Any methods disclosed herein include one or more steps or actions for performing the described method. One or more of the method steps and/or actions may be omitted from any of the methods disclosed herein. Moreover, any of the method steps and/or actions may be interchanged with one another. In other words, unless a specific order of steps or actions is required for proper operation of the embodiment, the order and/or use of specific steps and/or actions may be modified.

It will be understood that any number of different driving spring configurations and/or styles may be utilized with the general concepts disclosed in the present invention to reduce early stage drag forces that are imparted on an introducer needle within a given catheter system. For example, other driving spring configurations contemplated herein may include a helical spring configuration (not shown) that may be utilized to impart a force on an intermediate member to reduce early stage drag forces that are imparted on an introducer needle within a given catheter system.

Moreover, any number of ramp surfaces, configurations, and/or shapes are contemplated herein to achieve a desired force profile that will optimally reduce and/or normalize drag forces imparted on an introducer needle for a given catheter system, without departing from the spirit or scope of the present application. Thus, the number of ramp surfaces, plateaus, and stop bumps, as well as their configurations and/or shapes, can be varied in order to fine-tune any number of parameters including, but not limited to: (1) release timing for the driving spring; (2) the smoothness of the driving spring before/during release of the driving spring and/or during actuation of the driving spring along its full range of motion; (3) adjusting the maximum and/or minimum forces provided by the driving spring; (4) adjusting any transitional characteristics of the driving spring force as the driving spring transitions between a given maximum and minimum force; (5) adjusting an average force provided by the driving spring (e.g., either through adjusting an angle of a ramp and/or by adjusting a strength of the driving spring itself), etc.

It will also be noted that in at least some embodiments, a maximum driving force may be chosen that will not exceed the drag forces applied to the introducer needle by a given catheter system. In this manner, unintentional self-advancement of the catheter may be avoided, and/or advancement of the catheter at a more rapid rate than is expected by the clinician may also be avoided.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or − 10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A catheter assembly, comprising:
   an introducer needle coupled to a needle hub;
   an intermediate member comprising a contact surface disposed at a distal end of the intermediate member, the intermediate member configured to slidably receive the introducer needle therethrough;
   a catheter adapter body;
   a catheter projecting from a distal end of the catheter adapter body;
   a ramp member coupled to the needle hub, wherein the ramp member comprises a first ramp surface and a second ramp surface opposite the first ramp surface;
   a first resilient member and a second resilient member;
   a first bearing member configured to rotate with respect to the first resilient member; and
   a second bearing member configured to rotate with respect to the second resilient member, wherein the first bearing member is configured to engage the first ramp surface and the second bearing member is configured to engage the second ramp surface, wherein the first bearing member and the second bearing member impart a force on the first ramped surface and the second ramped surface, respectively, to urge the intermediate member in a distal direction relative to the needle hub, wherein the contact surface of the intermediate member is configured to engage a proximal surface of the catheter adapter body and urge the catheter adapter body in the distal direction relative to the needle hub.

2. The catheter assembly of claim 1, further comprising a driving spring, wherein the driving spring comprises the first resilient member and the second resilient member.

3. The catheter assembly of claim 1, wherein the first ramp surface comprises a concave surface portion, wherein the second ramp surface comprises another concave surface portion, wherein the first bearing member is disposed within the concave surface portion and the second bearing member is disposed within the another concave surface portion.

4. The catheter assembly of claim 1, wherein the first ramp surface comprises a plateau portion, wherein the second ramp surface comprises another plateau portion.

5. A method of inserting a catheter into a blood vessel of a patient through use of a catheter assembly comprising:
   an introducer needle coupled to a needle hub;
   an intermediate member comprising a contact surface disposed at a distal end of the intermediate member, the intermediate member configured to slidably receive the introducer needle therethrough;
   a catheter adapter body;
   a catheter projecting from a distal end of the catheter adapter body;

a ramp member coupled to the needle hub, wherein the ramp member comprises a first ramp surface and a second ramp surface opposite the first ramp surface;
a first resilient member and a second resilient member;
a first bearing member configured to rotate with respect to the first resilient member; and
a second bearing member configured to rotate with respect to the second resilient member, wherein the first bearing member is configured to engage the first ramp surface and the second bearing member is configured to engage the second ramp surface, wherein the first bearing member and the second bearing member impart a force on the first ramped surface and the second ramped surface, respectively, to urge the intermediate member in a distal direction relative to the needle hub, wherein the contact surface of the intermediate member is configured to engage a proximal surface of the catheter adapter body and urge the catheter adapter body in the distal direction relative to the needle hub;
the method comprising:
 inserting a distal end of the introducer needle within the blood vessel of the patient;
and
 advancing the intermediate member proximally relative to the introducer needle,
thereby:
 engaging the first resilient member and the second resilient member with the first ramp surface and the second ramp surface, respectively, to impart the force on the intermediate member and urge the intermediate member in the distal direction relative to the needle hub;
 engaging the contact surface of the intermediate member with the proximal surface of the catheter adapter body to urge the catheter adapter body in the distal direction relative to the needle hub; and
 urging the catheter coupled to the catheter adapter body in the distal direction relative to the introducer needle.

6. The method of claim 5, further comprising:
moving the needle hub and the introducer needle in a proximal direction relative to the catheter; and
withdrawing the introducer needle from the catheter.

7. The method of claim 5, further comprising a driving spring, wherein the driving spring comprises the first resilient member and the second resilient member.

8. The method of claim 5, wherein the first ramp surface comprises a concave surface portion, wherein the second ramp surface comprises another concave surface portion, wherein the first bearing member is disposed within the concave surface portion and the second bearing member is disposed within the another concave surface portion.

9. The method of claim 5, wherein the first ramp surface comprises a plateau portion, wherein the second ramp surface comprises another plateau portion.

* * * * *